United States Patent [19]

Fabian et al.

[11] Patent Number: 4,936,853
[45] Date of Patent: Jun. 26, 1990

[54] MODULAR KNEE PROSTHESIS

[75] Inventors: Dennis F. Fabian, Short Hills, N.J.; William C. Kim, Los Angeles, Calif.; Rick W. Basset, Los Fresnos, Tex.; Michael A. Jacobs, Baltimore, Md.

[73] Assignee: Kirschner Medical Corporation, Timonium, Md.

[21] Appl. No.: 295,845

[22] Filed: Jan. 11, 1989

[51] Int. Cl.⁵ .............................................. A61F 2/38
[52] U.S. Cl. .......................................... 623/20; 623/18
[58] Field of Search .................... 623/20, 18, 21–23

[56] References Cited

U.S. PATENT DOCUMENTS

| | | | |
|---|---|---|---|
| 4,209,861 | 7/1980 | Walker et al. | 623/20 |
| 4,213,209 | 7/1980 | Insall | 623/20 |
| 4,257,129 | 3/1981 | Volz | 623/20 |
| 4,298,992 | 11/1981 | Burstein et al. | 623/20 |
| 4,309,778 | 1/1982 | Buechel et al. | 623/20 |
| 4,714,474 | 12/1987 | Brooks et al. | 623/20 |

FOREIGN PATENT DOCUMENTS 2839093  3/1980  Fed. Rep. of Germany ........ 623/20

OTHER PUBLICATIONS

AMK Knee/Depuy.
Miller/Galante Brochure.

*Primary Examiner*—Ronald L. Frinks
*Attorney, Agent, or Firm*—Frost & Jacobs

[57] ABSTRACT

The present invention relates to an implantable knee joint prosthesis which is designed to replace the engaging surfaces of the femur and tibia of a dysfunctional human knee joint. In its most general form, the invention comprises an implantable knee joint prosthesis having a tibial stem portion, a tibial tray portion, an interchangeable modular articulating surface member which is removably attached to the tibial tray portion, and a femoral portion adapted to cooperatively bear upon the articulating surface. The invention also features a dual locking mechanism which attaches the articulating surface to the tibial tray portion by means of a locking lip and flange arrangement together with a locking screw which fits into the tibial stem portion.

6 Claims, 3 Drawing Sheets

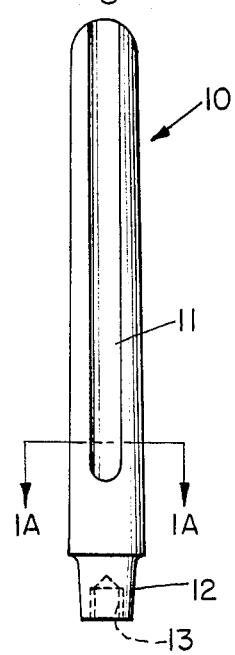
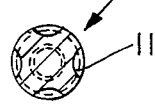
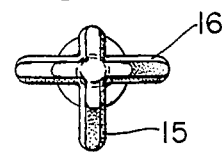
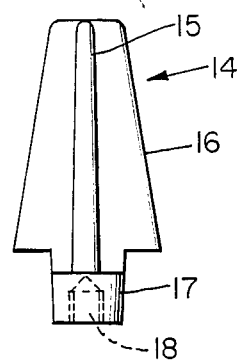
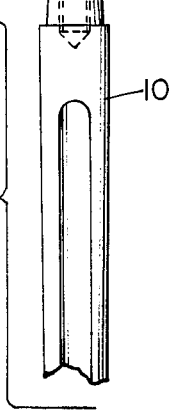
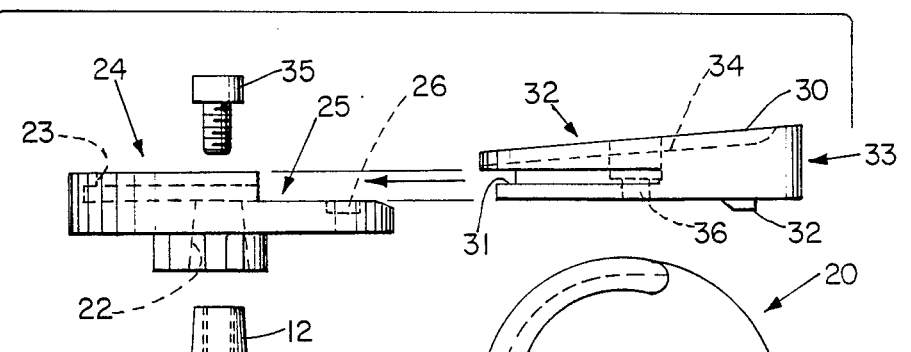
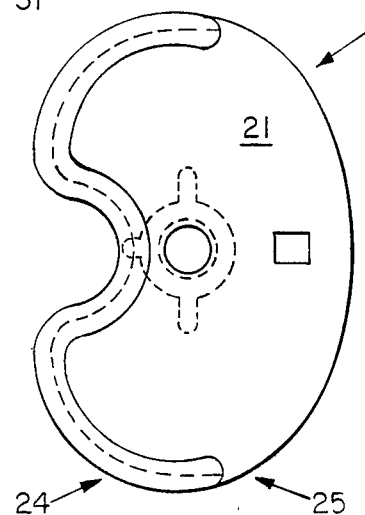

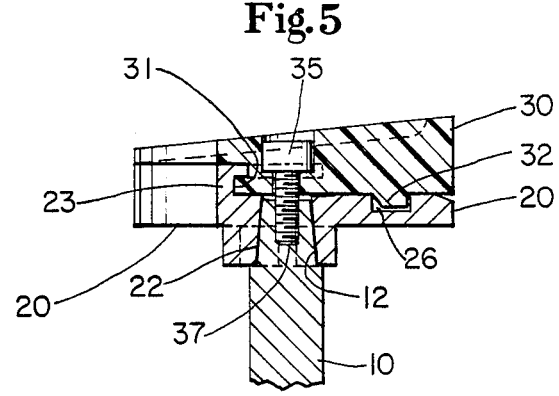
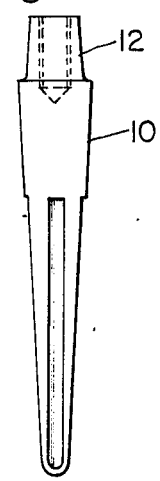
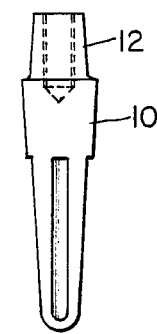
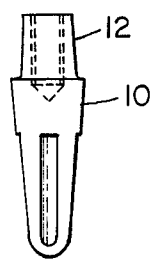

4,936,853

MODULAR KNEE PROSTHESIS

TECHNICAL FIELD

The present invention relates to implantable knee joint prostheses for replacement of the engaging surfaces of the femur and tibia of a dysfunctional human knee joint.

BACKGROUND

In the past, the design and development of total knee replacement prostheses for diseased and/or damaged human knees have typically been restricted to no more than three factory-assembled components; namely, the femoral, tibial and patellar replacement components. These devices have been designed to fit the anatomical variations and surgical needs of the largest possible segment of the eligible population while maintaining a manageable inventory of component parts. Such prior art designs typically incorporate plastic tibial articulating surfaces which are permanently assembled at a factory to a metal base plate having some configuration of a rigid, integral stem which extends down into the tibial plateau surface.

Due to the wide variations of natural, anatomical configurations of the human proximal tibia, the unpredictable bone quality of the tibial plateau and the varying degrees of deterioration resulting from arthritis, trauma, or failed previous prostheses, a need has existed for a versatile tibial prosthesis which can be custom fit to meet the needs presented by the above-described variables.

Also, because joint prostheses in general, and particularly knee replacements, are being implanted in patients with increasingly longer life expectancies, the need also exists for a prosthesis which allows for later replacement of a worn bearing surface without disturbing the components firmly affixed in or to the bones.

It is therefore an object of the present invention to provide an implantable knee joint prosthesis which allows several of its component parts to be mass produced while allowing a custom fit for each patient and his or her particular therapeutic need. It is also an object of the present invention to allow such custom fitting to be easily accomplished without sacrificing overall prosthesis quality and performance. This feature also provides the surgeon with a selection of a number of articulating/bearing surfaces with varying amounts of constraint, and congruency with the femoral component for patients with various degrees of soft tissues laxity which could not be preoperatively anticipated. The surgeon may therefore tailor the implant to better fit the patient's knee as it is found to exist and thereby decrease the probability that the knee prosthesis would require future adjustment, modification or replacement.

Finally, it is an object of the invention to provide a knee prosthesis which allows for later replacement of worn bearing surfaces without the necessity of disturbing and/or replacing those components of the prosthesis which have been and remain firmly affixed to their respective bones.

These and other advantages will become apparent to one of ordinary skill in the art in light of the following disclosure, drawings and claims.

SUMMARY OF THE INVENTION

The present invention relates to an implantable knee joint prosthesis which is designed to replace the engaging surfaces of the femur and tibia of a dysfunctional human knee joint. In its most general form, the invention comprises an implantable knee joint prosthesis having a tibial stem portion, a tibial tray portion, an interchangeable modular articulating surface member which is removably attached to the tibial tray portion, and a femoral portion adapted to cooperatively bear upon the articulating surface.

The present invention is intended to provide certain improvements over the prior art such as described in U.S. Pat. Nos. 4,209,861; 4,298,992; and 4,309,778, all of which are hereby incorporated herein by reference.

One feature of the present invention is to offer modular tibial stem configurations which can be affixed to the tibial tray component. The tibial stem portion and tibial tray portion may be permanently attached into an integral piece although it is preferable that the tibial stem portion, the tibial tray portion and the articulating surface member be removably attached to form a complete assembly. Such an arrangement facilitates easier implantation while allowing the interchange of articulating surface members of various dimensions.

When separate pieces, the tibial stem portion and the tibial tray portion may be removably attached by a self-locking Morse taper which uses a mechanical locking device such as a pin or bolt to maintain the tapered male end in the mating female taper. This is preferably done with the male side being on the proximal end of the stem and the mating female tapered aperture being in the underside of the tibial tray. A locking member holds the tibial tray portion (together with the modular articulating surface it holds) onto the tibial stem by fitting into the tibial stem portion. This member may be, for instance, a locking screw- which fits into threads in the tibial stem portion.

The tibial stem portions may be of various lengths and in various configurations, such as round or cruciate-shaped.

The taper and locking member construction therefore provide a dual locking mechanism.

The present invention also provides an interchangeable modular articulating surface member which is removably attached to the tibial tray portion. The articulating surface member may therefore be selected from a collection of such members having various thicknesses, dimensions and shapes, which can be interchangeably attached to the tibial tray portion to form a complete tibial plateau portion. This may be accomplished by any appropriate mechanical locking arrangement. One such arrangement is by the articulating surface member having a locking lip on the lower portion of one side which cooperatively fits into a locking lip on the corresponding side of the tibial tray which allows the articulating surface member to slide into its assembled position where a locking flange, appropriately located on the underside of the opposite side of the articulating surface member, locks into a groove located in a corresponding position on the corresponding opposite side of the tibial tray portion. It is preferred that the locking lips be located on the posterior side of the articulating surface member and the tibial tray portion and, accordingly, that the locking flange and groove be located, respectively, on the anterior sides of these two parts of the tibial plateau. As used herein, the term "tibial plateau" refers collectively to the tibial tray portion and the articulating surface member of the present invention, regardless whether the former is permanently or removably attached to the latter.

Together with the locking member, the locking lip arrangement allows the entire articulating surface member/tibial tray/tibial stem assembly to be locked together by a dual locking mechanism.

The present inventive prosthesis also comprises a femoral portion, attached to the distal portion of the femur, adaptively shaped to cooperatively bear upon the bearing surface of articulating surface member so as to produce a prosthesis which allows restored knee action.

DESCRIPTION OF THE DRAWINGS

The following figures, in which like reference numbers refer to like parts, describe some embodiments of the present invention.

FIG. 1 is an elevational view of a round, fluted modular tibial stem portion which may be used in accordance with the present invention.

FIG. 1a is a longitudinal view of the tibial stem portion shown in FIG. 1.

FIG. 2 is an elevational view of a cruciate-shaped modular tibial stem portion which may be used in accordance with the present invention.

FIG. 2a is a longitudinal view of the tibial stem portion shown in FIG. 2.

FIG. 3 is a planar view of the top side of a tibial tray portion which may be used in accordance with the present invention.

FIG. 4 is an exploded, elevational view of a tibial stem portion, tibial tray portion, articulating surface member, and locking screw showing their assembly in accordance with one embodiment of the present invention.

FIG. 5 is a cross-sectioned, elevational view showing the assembled components of FIG. 4 in accordance with one embodiment of the present invention.

FIG. 6 is an elevational view of several round, fluted tibial stem portions of different sizes which may be used, in accordance with the present invention.

DETAILED DESCRIPTION OF THE PREFERRED EMBODIMENT

Figure 7:
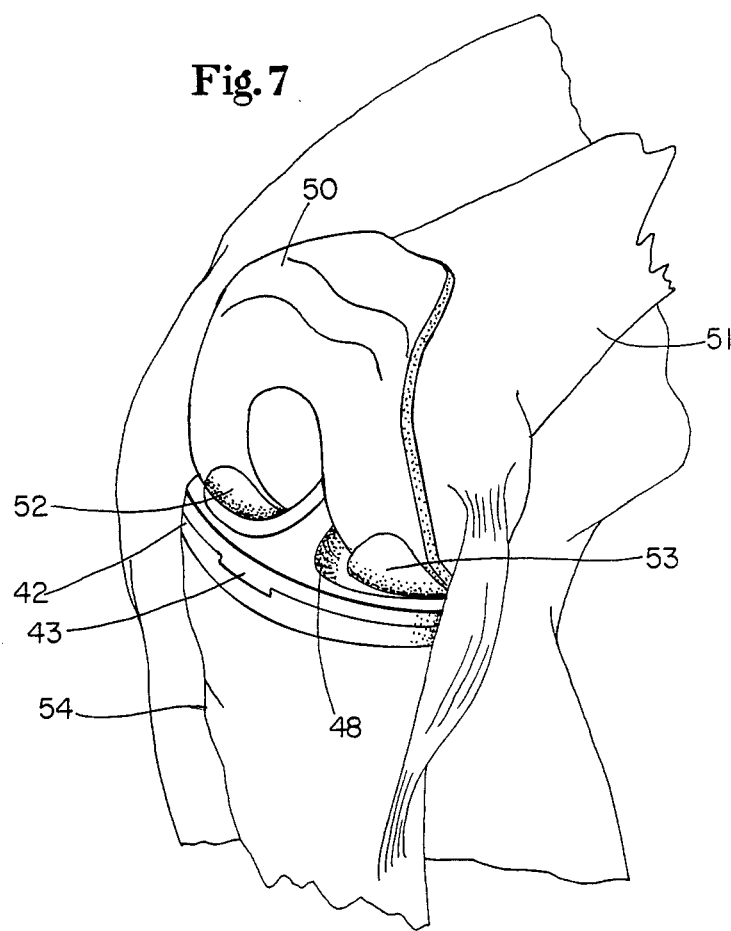
FIG. 7 is an environmental view showing a femoral portion of a knee prosthesis in operative contact with a tibial plateau in accordance with one embodiment of the present invention.

In accordance with and in furtherance to the above summary, FIG. 1 shows a rounded, tibial stem portion 10 having fluting 11 and Morse taper 12. Tibial stem portion 10 also contains aperture 13 which is adapted to accept a locking bolt or locking pin. FIG. 2 shows a cruciate tibial stem portion 14 having flanges 15 and 16. Morse taper 17 and aperture 18 are also shown, aperture 18 being adapted to accept a locking bolt or locking pin.

FIG. 3 shows the top side 21 of tibial tray portion 20 containing aperture 22 adapted to accept the Morse tapers 12 or 17 of the tibial stem portions 10 or 14, respectively.

FIG. 4 shows the component parts of the tibial portion of one embodiment of the present inventive prosthesis. Tibial stem 10 attaches to tibial tray portion 20 via Morse taper 12 fitting into aperture 22. Articulating surface member 30, containing bearing surface 34, is removably attached to tibial tray portion 20 by locking lip 31 located on one side 32 thereof, which slides horizontally into connective cooperation with locking lip 23 on the corresponding one side 24 of tibial tray portion 20. The tibial tray portion 20 and articulating surface member 30 are held in the assembled configuration by locking flange 32, located on the underside of the opposite side 33 of the articulating surface member, which fits into groove 26 located on the corresponding opposite 25 of the tibial tray portion.. It is preferred that the sides 24 and 32 be the posterior side of the prosthesis, while sides 25 and 33 be the anterior side of the prosthesis.

The tibial tray portion and articulating surface member are further locked in the assembled configuration and held to the tibial stem portion by locking screw 35 which fits through aperture 36 so as to seat below bearing surface 34. Locking screw 35 threads into a threaded aperture in the proximal end of the tibial item portion 10 (not shown).

FIG. 5 shows the tibial portion of the prosthesis, shown in FIG. 4, in the assembled configuration. In this view, it can be seen how locking lips 23 and 31 together with the locking flange 32 and groove 26 removably hold articulating surface member 30 to tibial tray portion 20 in the assembled configuration. Locking screw 35 threads into threaded aperture 37 in tibial stem portion 10 in order to provide a dual locking mechanical arrangement which further holds Morse taper, 21 into tapered aperture 22 to hold tibial tray portion 10 to the assembled tibial plateau.

A femoral portion used in accordance with the present invention is shown in environmental view in FIG. 7. In this figure, femoral portion 50 can be seen attached to the distal end of the femur 51. The femoral portion 50 contains dual articulating members 52 and 53 which bear upon articulating surface 48 of the articulating surface member 45 which is in turn held on tibial tray portion 42 connected to the tibia 54.

Finally, FIG. 6 shows the tibial stem portion of FIG. 1 in several sizes which may be used as the size and strength characteristics of the tibia varies from patient to patient.

Any appropriate materials known in the art may be used to make the component parts of the present inventive prosthesis. It is preferred that the tibial tray and stem portions, the femoral portion and its articulating surfaces, and locking screws be made of appropriate metal alloys such as those containing cobalt, chromium, titanium and/or molybdenum known in the art or other appropriate non-corroding and non-toxic materials. The articulating surface member is preferably made of the low friction plastics known in the art, such as those containing ultra-high molecular weight polyethylene, particularly ASTM F648-84.

Modifications and variations may be made to the above-described invention without departing from its spirit.

What is claimed is:

1. An implantable knee joint prosthesis comprising:
   (a) a tibial stem portion;
   (b) a tibial tray portion;
   (c) an interchangeable modular articulating surface member removably attached to said tibial tray portion;
   (d) a femoral portion adapted to cooperatively bear upon said articulating surface;
   wherein said tibial stem portion, said tibial tray portion and said articulating surface member are removably attachable into a complete assembly; and wherein said tibial stem portion is removably attached by a self-locking Morse taper having its male end on the proximal end of said tibial stem portion and its mating female taper in the underside of said tibial tray portion.

2. An implantable knee joint prosthesis according to claim 1 wherein said interchangeable modular articulating surface member is selected from a collection of at least two such members of various dimensions.

3. An implantable knee joint prosthesis according to claim 1 wherein said articulating surface member is removably attached to said tibial tray portion by means of a locking lip on the lower portion of one side of said articulating surface member which is slid horizontally into connective cooperation with a locking lip on the corresponding side of said tibial tray portion, said tibial tray portion and said articulating surface member being locked in an assembled position by means of a locking flange, located on the underside of the opposite side of said articulating surface member, fitting into a groove located on the corresponding opposite side of said tibial tray portion, and by means of a locking member passing through said articulating surface member and said tibial tray portion into said tibial stem portion.

4. An implantable knee joint prosthesis according to claim 3 wherein said one side of said tibial tray portion and said articulating surface member is the posterior side and wherein said opposite side of said tibial tray portion and said articulating surface member is the posterior side.

5. An implantable knee joint prosthesis according to claim 3 wherein said locking member is a locking screw which fits into threads in said tibial stem portion.

6. An implantable knee joint prosthesis comprising:
 (a) a tibial stem portion;
 (b) a tibial tray portion removably attached to said tibial stem portion;
 (c) an interchangeable modular articulating surface member removably attached to said tibial tray portion;

wherein said tibial stem portion is attached to said tibial tray portion by a self-locking Morse taper having its male end on the proximal end of said tibial stem portion and its mating female tapered aperture in the underside of said tibial tray portion; and wherein said articulating surface member is removably attached to said tibial tray portion by means of a locking lip on the lower portion of the posterior side of said articulating surface member which is slid horizontally into connective cooperation with a locking lip on the corresponding posterior side of said tibial tray portion, said tibial tray Portion and said articulating surface member being locked in an assembled position by means of a locking flange, located on the underside of the anterior side of said articulating surface member, fitting into a groove located on the corresponding anterior side of said tibial tray portion, and by means of a locking screw which passes through said articulating surface member and said tibial tray portion into threads in said tibial stem portion.

* * * * *